United States Patent [19]

McGinnis

[11] Patent Number: 4,559,940

[45] Date of Patent: Dec. 24, 1985

[54] RESUSCITATION APPARATUS

[76] Inventor: Gerald E. McGinnis, 131 Kelvington Dr., Monroeville, Pa. 15146

[21] Appl. No.: 577,542

[22] Filed: Feb. 6, 1984

[51] Int. Cl.⁴ .......................................... A61M 16/00
[52] U.S. Cl. ......................... 128/206.26; 128/206.29; 128/207.14; 128/202.28
[58] Field of Search ...................... 128/200.26, 207.14, 128/207.16, 202.28, 202.29, 203.11, 206.24, 206.29, 207.15, 206.26

[56] References Cited

U.S. PATENT DOCUMENTS

| 4,112,936 | 9/1978 | Blachly | 128/207.14 |
| 4,446,864 | 5/1984 | Watson et al. | 128/202.28 |
| 4,449,526 | 5/1984 | Elam | 128/206.24 |

FOREIGN PATENT DOCUMENTS

| 1348518 | 12/1963 | France | 128/207.14 |
| 23063 | 4/1962 | German Democratic Rep. | 128/206.29 |
| 840638 | 7/1960 | United Kingdom | 128/206.24 |
| 889130 | 2/1962 | United Kingdom | 128/206.29 |

Primary Examiner—Henry J. Recla
Attorney, Agent, or Firm—Carothers & Carothers

[57] ABSTRACT

A resuscitation apparatus including improved mouth and nasal seal means and improved gas flow passage maintaining configurations.

19 Claims, 5 Drawing Figures

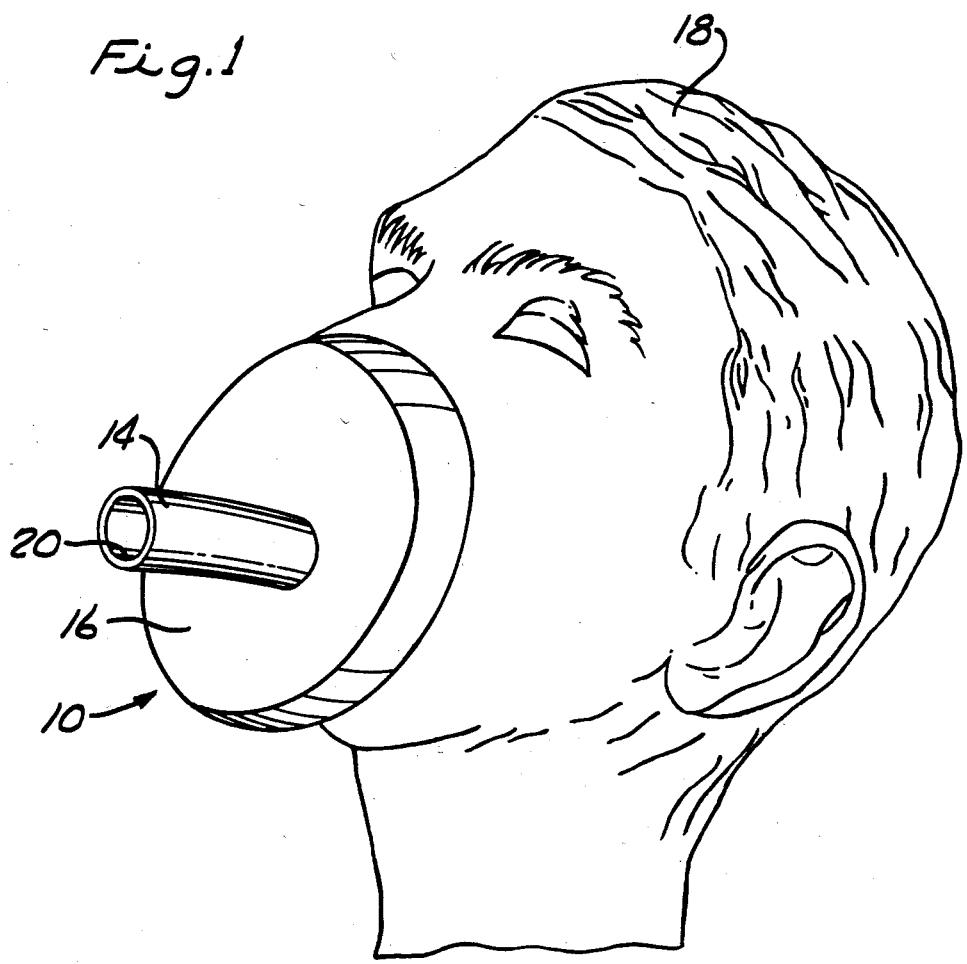
Fig.1
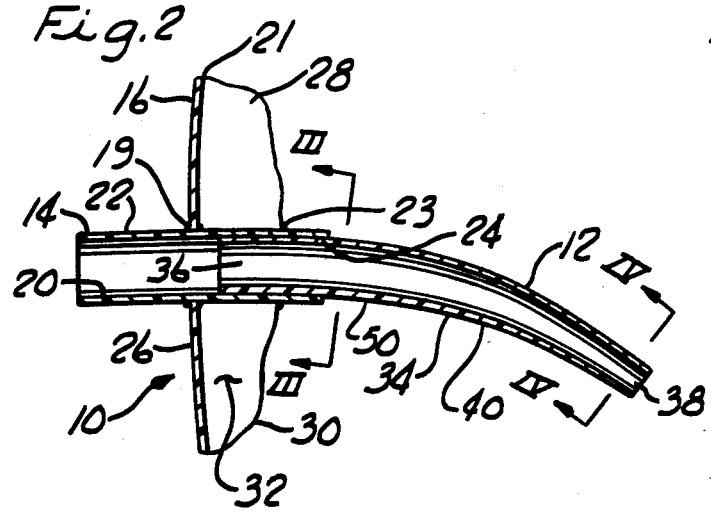
Fig.2
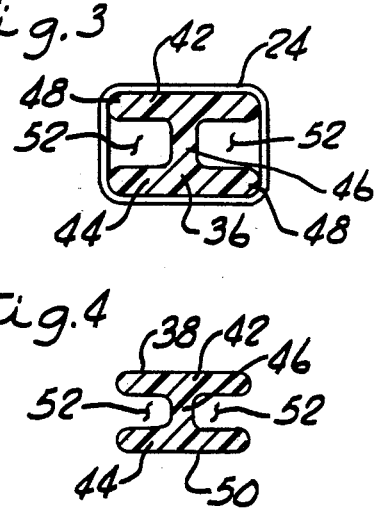
Fig.3
Fig.4

RESUSCITATION APPARATUS

The prior art of medical gas administering equipment is replete with examples of apparatus for providing efficient transfer of breathing air or other medical gas from external supply equipment to the patient. Such apparatus typically includes a tube such as an endotracheal tube which is adapted to be inserted into the airway of the patient whereupon an inflatable cuff is inflated to seal the airway thus ensuring delivery of the gas being administered to the lungs of the patient.

In those emergency situations requiring immediate administration of breathing air, oxygen or other medical gas, the very life of the patient may well depend upon the efficiency of the apparatus by which the needed gas is administered. For example, in those emergency situations where the patient's spontaneous breathing has ceased and breathing must be artifically stimulated, the technique of cardiopulmonary resuscitation (CPR) is considered to be one suitable means of artificial breathing stimulation. In CPR practice, the CPR practitioner forces air into the patient's lungs by placing his mouth over that of the patient and forcing the air from his own lungs, and subsequently allowing the inherent resiliency of the patient's chest components to force the air out. By this procedure, which involves considerably more technique than above described, particularly related to cardiac massage, the patient's breathing is artificially maintained and his oxygen needs thus satisfied. Without the artificial stimulation, the patient could very well suffer severe brain damage or other consequences of oxygen starvation.

In the practice of CPR and other techniques of emergency air or medical gas administration, various problems have long been recognized. For example, in CPR it is essential that an effective gas tight seal be formed about the nose and mouth of the patient to control gas transfer and to thereby ensure that the emergency gas is actually getting to the patient's lungs rather than escaping to the atmosphere. It is equally important to ensure that the patient's airway remains open and is not blocked by foreign matter or the patient's tongue. More specifically, it is most important to guard against the possibility of the patient swallowing his tongue and thereby blocking his breathing passage. For the conscious or semi-conscious patient, any gas administering apparatus which is inserted into the upper airway of the patient must be of such a configuration to avoid, to the extent possible, stimulation of the patient's gag reflex. Finally, in the emergency adminstration of medical gas or air, the equipment utilized serves best if it is simple of design, easy to use, reliable, sturdy, light in weight and compact.

The present invention contemplates an improved resuscitation apparatus which is inserted into the mouth of a patient for the purpose of administering breathing air or medical gas. The invention in one preferred embodiment includes a gas delivery tube having associated therewith a simplified and reliable air bladder seal which seals off the area of the patient's face encompassing the nasal passages and the perimeter of his mouth when the tube is inserted into the mouth. The apparatus also includes an elongated, curved and formed beam which extends into the patient's mouth and throat. The beam serves to depress the tongue, and prevents obstruction of the patient's airway. Additionally, the beam provides a bite block upon which the patient may bite. Such biting may occur as a spontaneous response to pain or the presence of the gas delivery apparatus in the mouth, for example.

The invention is compact and light in weight thus permitting its convenient inclusion in emergency equipment kits whereby the apparatus can be made readily available for emergency use without difficulty and without any significant trade-off or choice as between the various articles of emergency care that might be included in such an emergency kit.

Accordingly, it is one primary object of this invention to provide an improved air or gas administration apparatus.

Another object of the invention is to provide an improved resuscitation assisting apparatus including an air inlet means, a tongue depresser and mouth and nasal passage seal specifically adapted for practice of CPR and other emergency resuscitation procedures.

Other objects and advantages appear in the following description and claims.

The accompanying drawings show, for the purpose of exemplification without limiting the invention or the claims thereto, certain practical embodiments illustrating the principles of this invention wherein:

FIG. 1 is a perspective view of the apparatus of the invention in use;

FIG. 2 is a longitudinal sectional view of the apparatus of the invention;

FIG. 3 is a section taken on line III—III of FIG. 2;

FIG. 4 is a section taken on line IV—IV of FIG. 2; and

Figure 5:
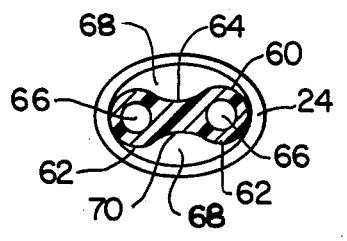
FIG. 5 is a section similar to FIG. 3 of an alternative embodiment of the invention.

There is generally indicated at 10 in FIGS. 1 and 2 a resuscitation apparatus according to one presently preferred embodiment of the present invention. Resuscitation apparatus 10 includes an elongated beam portion 12 which is secured longitudinally adjacent an elongated air inlet portion 14, and a face seal portion 16 located intermediate the longitudinal ends of the apparatus 10 and preferably located proximate the connection between beam portion 12 and air inlet tube portion 14.

In practice the apparatus 10 is utilized by insertion of the beam portion 12 into the mouth and throat of the patient 18 such that seal portion 16 forms a continuous surface seal over the mouth and nares of the patient 18 as shown in FIG. 1. Hand pressure may be employed to maintain the seal about the patient's mouth and nose while the medical gas source, an administrator of CPR for example, supplies the needed gas via the outer open end of 20 of tube portion 14 to the patient 18. The apparatus 10 provides for easier operation because the nasal passages are sealed at the nares whereas prior apparatus generally attempted seals at the bridge of the nose.

Apparatus 10 structurally comprises an elongated flexible inlet tube 22 of resilient plastic, for example having the open outer end 20 of an open inner end 24. Tube 22 is of sufficiently large interior cross sectional area to permit sufficient gas flow rates at low pressure to satisfy the gas delivery requirements of the particular procedure being applied. The outer open end 20 of tube 22 may include any suitable fitting or formed portion (not shown) to facilitate its connection to a desired source of supply, or for its use by a CPR administrator.

Tube 22 is encompassed intermediate its ends by seal portion 16 which includes a flexible but self-supporting backup disk 26 encompassing tube 22 and sealingly connected thereto as at 19 to form one wall of an air seal bladder or cuff 28. Air seal bladder 28 is comprised of the disk 26 and a flexible membrane 30 of resilient plastic for example which encompasses tube 22 and is sealed thereto as at 23, and is also connected to the periphery of disk 16 as at 21 by a continuous, circumferentially extending sealed connection. Any suitable adhesive bonding system or plastic molding technique may be utilized to secure the seal portion 16 in encompassing relationship about tube 22 and to seal the joints therebetween whereby the space 32 is a completely closed volume having generally the form of a donut. A volume of air is permanently sealed within a space 32 bounded by disk 26, membrane 30 and the tube 22 passing therethrough to provide a cushioned sealing means for sealing the mouth and nasal passage of a patient. More specifically, the air volume within space 32 is limited to a volume such that at ambient temperatures the membrane 30 is not distended or stretched taut but rather is loose and flexible. That is, the membrane 30 does not have an inflated balloon-like appearance. In use, manual pressure is applied via hand pressure upon disk 16 against the mouth and nose area of the patient's face. In response, the loose membrane 30 conforms to the facial contours of that portion of the patient's face in confronting relation therewith and the air within space 32 is thus distributed and pressurized, to the extent of the manual pressure applied, to provide a continuous surface seal throughout the mutually contiguous surface areas of membrane 30 and the portions of the patient's face contacted thereby. In effect, substantially the entire surface area of membrane 30 is formed and sealed against the confronting portions of the patient's face to thereby provide a superior seal which is quite readily and conveniently maintained.

Beam portion 12 comprises an elongated curved and formed beam 34, shown as an I-beam configuration in FIGS. 2-4, and formed of relatively rigid molded plastic or the like. Beam 34 includes a relatively enlarged end portion 36, a relatively smaller end portion 38, and a generally tapering elongated intermediate portion 40 extending longitudinally between end portions 36 and 38. The I-beam cross sectional configuration of beam 34 adjacent end portion 36 (FIG. 3) includes upper and lower flange portions 42, 44, respectively, and an integral, vertically extending web portion 46 extending therebetween. The laterally outer extremities 48 of each of flange portions 42, 44 are smoothly rounded to minimize patient discomfort, minimize stress concentrations, and improve ease of manufacture by plastic molding processes.

The smaller end portion 38 of beam 34 (FIG. 4) is similar in cross sectional configuration the opposite end portion 36 but is of relatively reduced lateral dimensions to permit the end portion 38 to be received into the upper airway of the patient. The intermediate portion 40 of beam 34 is smoothly tapered between the illustrated end portion configurations and is curved downwardly to conform to the mouth and throat areas of the patient and to fit comfortably therein.

The enlarged end portion 36 of beam 34 is received within the inner open end 24 of tube 22 and maintained therein by such suitable means as an adhesive bonding agent or the elastic resiliancy of tube end portion 24 by which tube portion 24 circumferentially grips the beam end portion 36, or by integral molding techniques. The rigid beam end portion 36 encompassed by tube end 24 provides a bite block on which the patient may bite in response to pain or discomfort.

The lower surface 50 of flange 44 provides throughout the length of beam 34 a tongue depressor function which assures the patient's tongue is restrained from interfering with the gas administration process. Particularly in this regard it is noted that the invention effectively guards against the possibility of the unconscious patient swallowing his tongue.

Between flanges 42 and 44 on either side of web 46 there are formed longitudinally extending, laterally outwardly open air passages or channels 52. The channels 52 extend throughout the length of beam 34, tapering from a relatively enlarged cross sectional area adjacent the end portions 36 to a relatively smaller cross sectional area adjacent end portion 38. Generally in proportion to the overall taper of beam 34 throughout its length. The configuration of the air channels 52 ensures that a clear air flow passage of sufficient air flow capacity at low pressure will be maintained through the mouth of the patient and into his throat. Even if the patient's tongue were to assume a position tending to block one of channels 52, it could not possibly block both channels 52 and one would thus remain open.

In an alternative embodiment of the invention as shown in FIG. 5, an elongated curved, double tube structure 60 generally of a figure-light cross sectional configuration is substituted for beam 34. Tube structure 60 includes a pair of integrally formed tube portions 62 joined by a bridging portion 64. Alternatively, the tube portions 62 may be separate tubes which are bonded together side-by-side by any suitable bonding agent. One end of tube structure 60 is received within tube end portion 24 in a manner entirely similar to that described hereinabove with respect to beam 34. By this embodiment, internal air flow passages extending along tube structure 60 are defined with tube portions 62 as indicated at 66. In addition, laterally open outer air passages 68 are also defined by the concave depressions 70 between the tube portions 62. Accordingly this embodiment, like that first described, also provides a pair of laterally open air flow passages having similar functional capability and offering similar benefits and advantages. Of course it is to be understood that the cross sectional form of tube structure 60 is substantially the same throughout its length, although proportions and dimensions thereof may differ from one longitudinal end thereof to the other.

The invention as described permits CPR or other emergency gas administration technique to be performed with improved ease and efficiency. Among other advantages offered, the apparatus is simple in construction, inexpensive, light weight, compact and highly utilitarian. Notwithstanding the description hereinabove of a particular preferred embodiment of the invention, it will be appreciated that the invention is capable of various modifications and alternative embodiments. For example, the specific materials of construction may be selected from a variety of material having the described requisite properties; in seal portion 16 the air in space 32 might be replaced by water or other suitable fluid or the seal portion might alternatively incorporate a resiliently deformable medium such as a mass of closed cell foam in the form of a foam pad; a head band may be included to maintain seal 28 in sealing contact with the patient's face, and the like.

These and other embodiments and modifications having been envisioned and anticipated by the inventor, the invention is to be construed as broadly as permitted by the scope of the claims appended hereto.

I claim:

1. In a gas delivery apparatus including a gas flow conducting means and adapted for delivery of medical gas to a patient from an external gas source through the patient's mouth via the gas flow conducting means which extends into the patient's mouth and further including seal means adapted to seal the patient's mouth and nasal openings from the ambient atmosphere, the improvement comprising:

said seal means comprising deformable means encompassing said gas flow conducting means and including a formable exterior wall disposed for confronting relationship with the patient's face throughout an area of contact having an outer perimeter which encompasses the patient's mouth and nasal openings such that said area of contact extends continuously intermediate said gas flow conducting means and said outer perimeter, said formable exterior wall being adapted to conform to the patient's facial contours throughout said area of contact to provide a continuous surface seal throughout said area of contact for sealing of the patient's mouth and nasal openings from the ambient atmosphere.

2. The improvement as claimed in claim 1 wherein said deformable means includes a fluid contained within a bladder and said exterior wall is an exterior wall of said bladder.

3. The improvement as claimed in claim 2 wherein said fluid is water.

4. The improvement as claimed in claim 2 wherein said fluid is a gas.

5. The improvement as claimed in claim 2 wherein the volume of fluid contained within said bladder is less than the volume of fluid required to distend said exterior wall.

6. The improvement as claimed in claim 2 wherein said deformable means includes a mass of closed cell foam and said exterior wall is an exterior wall of said mass.

7. A medical gas administering apparatus adapted for administering gas to a patient comprising:

an elongated body;

said elongated body including an elongated formed beam which is adapted to be received within the mouth and throat of such a patient with an outer end portion of said beam extending outwardly of the patient's mouth;

said beam being formed to define at least one laterally open gas flow passage extending longitudinally thereof for permitting gas flow within the mouth and throat and to the airway of such a patient;

said body including gas flow conducting means located adjacent said outer end portion of said beam;

said gas flow conducting means defining a gas flow passage which communicates with said at least one laterally open passage adjacent said outer end portion of said beam for delivery of gas to such a patient;

seal means comprising a deformable means which encompasses said elongated body intermediate the longitudinal ends thereof and includes a formable exterior wall disposed for confronting relationship with the patient's face throughout an area of contact having an outer perimeter which encompasses the patient's mouth and nasal openings such that said area of contact extends continuously intermediate said elongated body and said outer perimeter whereby said formable exterior wall is adapted to conform to the patient's facial contours throughout said area of contact to provide a continuous surface seal throughout said area of contact for sealing of the patient's mouth and nasal openings from the ambient atmosphere.

8. The apparatus as claimed in claim 7 wherein said gas flow conducting means is an elongated open ended tube means.

9. The apparatus as claimed in claim 8 wherein said outer end portion of said beam is received within one open end of said tube means.

10. The apparatus as claimed in claim 7 wherein said beam defines a pair of laterally open gas flow passages.

11. The apparatus as claimed in claim 10 wherein said pair of laterally open gas flow, passages are laterally opposed gas flow passages.

12. The apparatus as claimed in claim 11 wherein said beam is generally of an I-beam cross sectional configuration.

13. The apparatus as claimed in claim 11 wherein said beam is generally of a figure-eight cross sectional configuration.

14. The apparatus as claimed in claim 7 wherein said seal means includes a formable medium having an exterior wall portion adapted to be located for confronting relationship with the face of such patient.

15. The apparatus as claimed in claim 14 wherein said formable medium is a fluid contained within a bladder and said exterior wall portion is an exterior wall of said bladder.

16. The apparatus as claimed in claim 15 wherein said fluid is a gas.

17. The apparatus as claimed in claim 15 wherein said fluid is water.

18. The apparatus as claimed in claim 14 wherein said formable medium is a mass of closed cell foam and said exterior wall portion is an exterior wall of said mass.

19. The apparatus as claimed in claim 15 wherein the volume of said fluid within said bladder is less than the volume required to distend said exterior wall.

* * * * *